United States Patent
Posey

(10) Patent No.: US 11,748,689 B2
(45) Date of Patent: Sep. 5, 2023

(54) END-TO-END VACCINE DELIVERY SYSTEM AND METHOD OF DELIVERY AND POST-DELIVERY TRACKING

(71) Applicant: Tina Posey, Jersey City, NJ (US)

(72) Inventor: Tina Posey, Jersey City, NJ (US)

(*) Notice: Subject to any disclaimer, the term of this patent is extended or adjusted under 35 U.S.C. 154(b) by 0 days.

(21) Appl. No.: 17/479,476

(22) Filed: Sep. 20, 2021

(65) Prior Publication Data

US 2022/0092529 A1     Mar. 24, 2022

Related U.S. Application Data

(60) Provisional application No. 63/080,360, filed on Sep. 18, 2020.

(51) Int. Cl.
| | | |
|---|---|---|
| *G06Q 10/0832* | (2023.01) | |
| *G06Q 10/0833* | (2023.01) | |
| *G16H 40/67* | (2018.01) | |
| *F25D 29/00* | (2006.01) | |
| *G06F 21/62* | (2013.01) | |

(52) U.S. Cl.
CPC ......... *G06Q 10/0832* (2013.01); *F25D 29/00* (2013.01); *G06F 21/6245* (2013.01); *G06Q 10/0833* (2013.01); *G16H 40/67* (2018.01); *F25D 2700/12* (2013.01)

(58) Field of Classification Search
CPC ........... G06Q 10/0832; G06Q 10/0833; G06Q 10/083
See application file for complete search history.

(56) References Cited

U.S. PATENT DOCUMENTS

| | | | |
|---|---|---|---|
| 6,875,486 B2* | 4/2005 | Miller | B65D 81/18 |
| | | | 428/34.3 |
| 2007/0150312 A1* | 6/2007 | Schmidt | G06Q 10/10 |
| | | | 705/26.1 |
| 2018/0150613 A1* | 5/2018 | Bossi | G16H 20/13 |
| 2018/0353379 A1* | 12/2018 | Chou | A61J 1/165 |
| 2020/0347209 A1* | 11/2020 | Takacs | C08L 15/02 |
| 2020/0410446 A1* | 12/2020 | Rahilly | G07F 17/0092 |
| 2022/0051276 A1* | 2/2022 | Zelocchi | G16H 30/40 |
| 2022/0180299 A1* | 6/2022 | Väin | B60P 1/48 |

OTHER PUBLICATIONS

World Health Organization, "How to Monitor Temperatures in the Vaccine Supply Chain," Published by www.who.int, Jul. 2015, Retrieved from http://apps.who.int/iris/bitstream/handle/10665/183583/WHO_IVB_15.04_eng.pdf (Year: 2015).*

* cited by examiner

*Primary Examiner* — Rupangini Singh
*Assistant Examiner* — Bryan J Kirk
(74) *Attorney, Agent, or Firm* — Law Office of Mark Brown, LLC; Christopher M. DeBacker

(57) ABSTRACT

An end-to-end vaccine supply chain for distribution, tracking, delivery, implementation, and post-delivery data collection and processing. A supply chain is monitored by ensuring proper cold-chain distribution protects the vaccine from manufacturer all the way to delivery to a patient. Equipment would include a cold box integrated with sensors for monitoring temperature and ensuring that the box is not tampered with anywhere in the delivery chain. Back-end delivery tracking and post-delivery monitoring software systems provide up to date notifications to relevant parties of vaccine safety and other information.

13 Claims, 5 Drawing Sheets

END-TO-END VACCINE DELIVERY SYSTEM AND METHOD OF DELIVERY AND POST-DELIVERY TRACKING

CROSS-REFERENCE TO RELATED APPLICATION

This application claims priority in U.S. Provisional Patent Application No. 63/080,360 Filed Sep. 18, 2020, which is incorporated herein by reference.

BACKGROUND OF THE INVENTION

1. Field of the Invention

The present invention relates generally to a vaccine tracking and delivery system and method for use thereof, and more specifically to a complete end-to-end process and delivery of vaccines including security during transport and post-vaccination data collection.

2. Description of the Related Art

A global pandemic of the magnitude of the 2020 Covid-19 pandemic has not been experienced. It affects almost every aspect of our lives, including major health concerns and risk of death without a vaccine or accelerated efficient methods to find vaccine as well as get that vaccine to everyone worldwide. Globally, this situation is affecting our mortality, health, financial markets, socialization, and mental health. Existing systems may assist in the process of getting the vaccines to people who need them worldwide through an end-to-end process in a less costly and more efficient way, as well as component parts to make the process most efficient. However, no existing systems are providing completely secure end-to-end vaccine delivery and post-vaccination tracking in as efficient and secure manner as possible.

Heretofore there has not been available a system or method for an end-to-end vaccine delivery system with the advantages and features of the present invention.

BRIEF SUMMARY OF THE INVENTION

The present invention generally provides an end-to-end vaccine supply chain for distribution, tracking, delivery, implementation, and post-delivery data collection and processing. A supply chain is monitored by ensuring proper cold-chain distribution protects the vaccine from manufacturer all the way to delivery to a patient. Equipment would include a cold box integrated with sensors for monitoring temperature and ensuring that the box is not tampered with anywhere in the delivery chain.

Currently, hospitals use vaccine refrigerators which have high initial costs as well as very expensive ongoing maintenance requirements. These refrigerators are required at each vaccination site, and do not allow for ease of travel. The cold box of the present invention is intended to replace the need for such refrigerators at all sites, allowing for safe and easy delivery of vaccines at locations which may not have access to power or proper refrigeration.

The cold box has a coating on the exterior to help reduce heat absorbed from the environment. Several layers of temperature-controlled insulating material helps to further ensure proper temperature is maintained. A refrigerant gel material makes up the inner-most layer of the box. These layers work together to keep the box cool for a minimum of 36 continuous hours to maximum 48 continuous hours at a temperature suitable for hospital grade and vaccine temperature compliance. An embodiment of the present invention could be capable of maintaining 32 degrees Fahrenheit temperatures for at least 36 hours. Another embodiment could be capable of maintaining −20 degrees Fahrenheit temperatures for up to 24 hours.

The box is designed to be collapsible after use for ease of transport to both developed and emerging markets in a mass-vaccine situation. The box will also help to establish vaccine delivery in remote areas and warmer climates.

A temperature sensor constantly monitors temperature within the box and reports the temperature constantly to the live monitoring system. The temperature sensor also works in conjunction with a IoT sensor designed for tamper resistance monitoring. In areas of the world, especially in pandemic situations, there could be security risks resulting in tampering with vaccines being delivered. By providing temperature monitoring and tamper detection, the delivery system will ensure that vaccines arrive in a safe manner and that damaged or tampered-with vaccines are not given to patients. The box could be fitted with a solar panel for providing power for the various sensors and monitoring devices.

Proper chain of custody tracking ensures that the vaccine is properly handled as it is transferred from the manufacturer to the patient for final application.

Post-delivery monitoring also provides additional important follow-up data which can help track and ensure proper notification in an attempt to provide continued knowledge and understanding of success or failure of current and future mass-vaccine efforts. The tracking and reporting necessarily must provide security and privacy-protection in all data collected from patients. This would include all privacy rules, such as HIPAA, PII, and other privacy systems in other countries. Multiple layers of cyber protection, including mobile data would be used. Data would be collected using codes and vaccinated person PII input, tracing post-vaccine for results, and coded identifiers to be provided by patients post-vaccine to help track success or failure of the vaccine. Post vaccine data is to be continuously monitored for cyber protection.

BRIEF DESCRIPTION OF THE DRAWINGS

The drawings constitute a part of this specification and include exemplary embodiments of the present invention illustrating various objects and features thereof.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

II. Preferred Embodiment End-to-End Vaccine Delivery System 2

Figure 1:
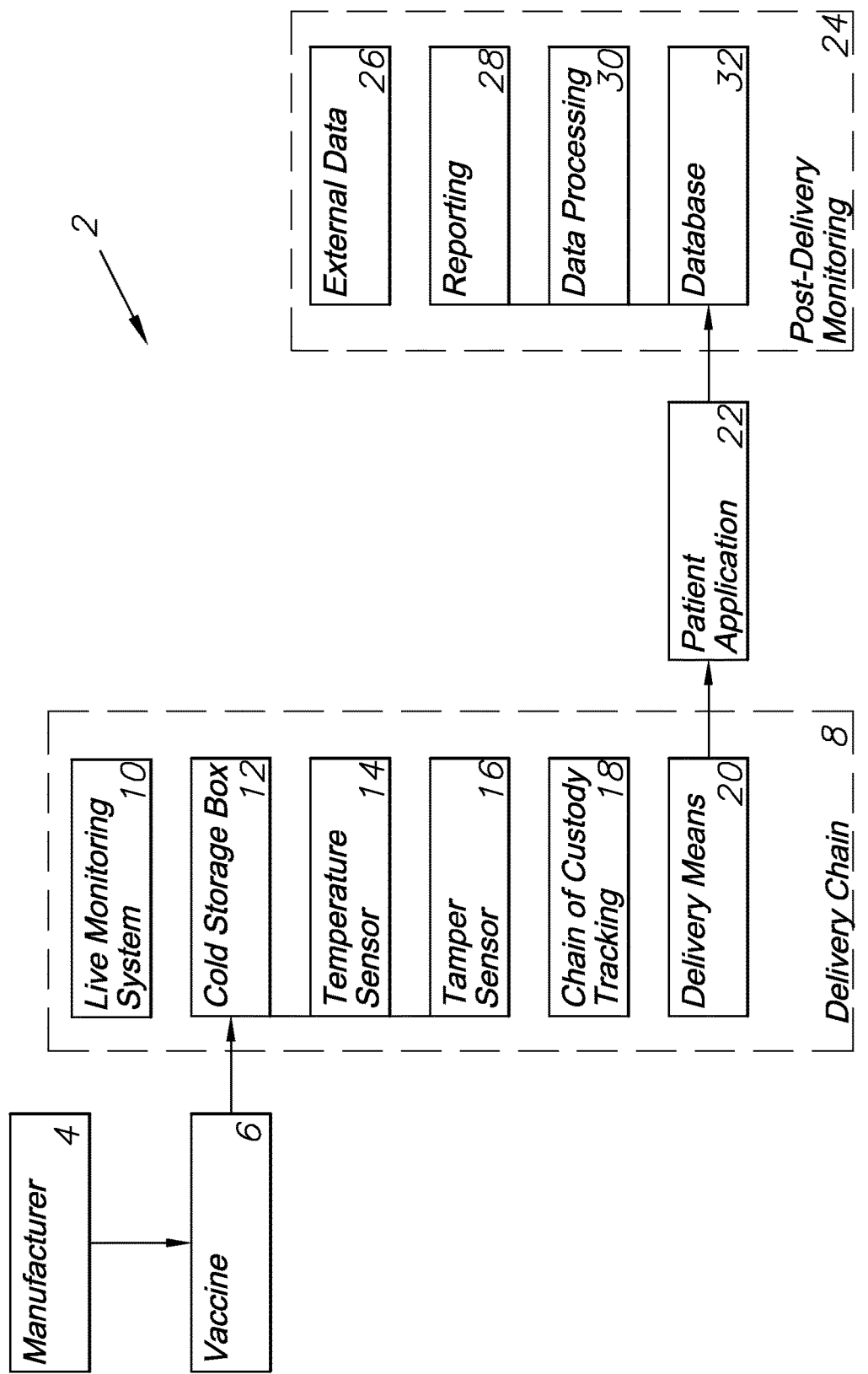
FIG. 1 is a block diagram showing the relationship between elements of the present invention.
Figure 2:
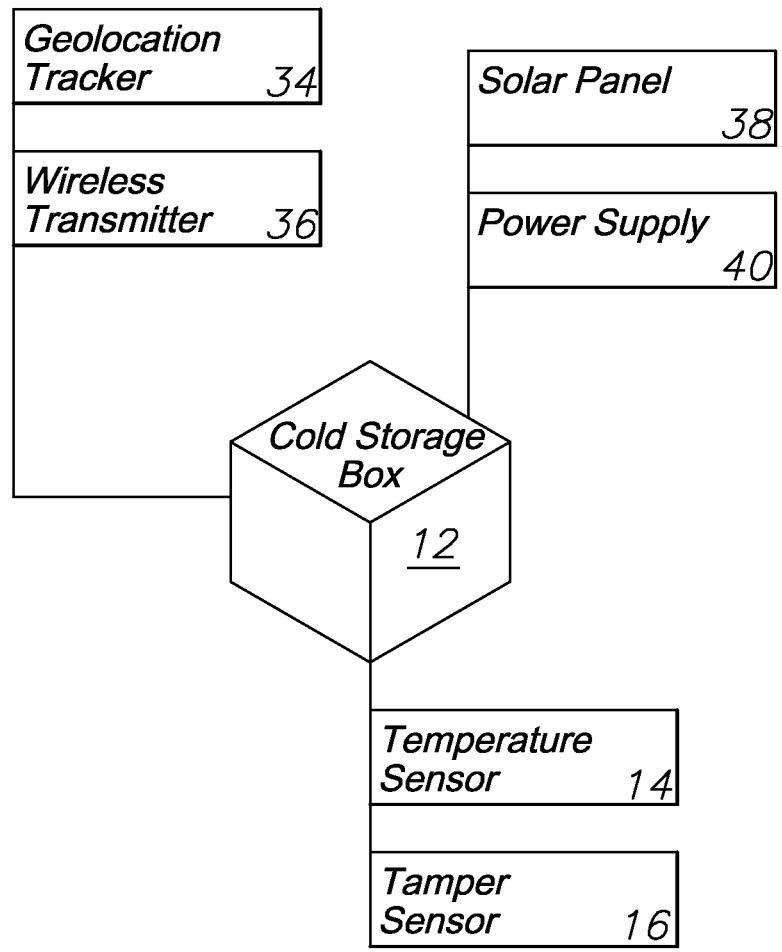
FIG. 2 is a diagram of a cold box element of the present invention including components thereof.

As shown in FIG. 1, the present invention provides an end-to-end vaccine delivery and monitoring system 2 including post-delivery data tracking and processing system 24. The manufacturer 4 who manufactures the vaccine 6 places the vaccine into the delivery chain 8, which may include a cold storage box 12 with temperature sensor 14 and tamper sensor 16. This box 12 ensures the vaccine 6 is kept at appropriate temperatures during transport and delivery to the patient where it is applied. The box 12, as shown in FIG. 2, is made of several layers of insulating and heat-resistant materials, including a refrigerant gel layer, which will keep the vaccine at an appropriate temperature for at least thirty-six hours. A version could be prepared for sub-zero degree temperatures, including maintaining a temperature of minus-twenty degrees Fahrenheit for twenty-four hours.

The live monitoring system 10 is a standard computerized tracking system for monitoring the chain of custody 18 and constant location of the vaccine 6 about the delivery chain 8. Any standard form of package tracking should suffice, but more secure means of tracking may be employed, such as constant GPS tracking.

Once the vaccine is delivered via a delivery means 20 at the patient application 22 site, the post-delivery monitoring system 24 will track data from external sources 26, internal sources, and potentially even from the patient. The post-delivery monitoring system 24 includes a reporting function 28 to allow it to report to the patient or other parties when issues may arrive. The data processing computer 30 behind the post-delivery monitoring system 24 includes a data storage database 32 for collecting and analyzing the various data from the various sources.

The box 12 may include a power supply 40, such as a battery. A solar panel 38 can also be included which will provide additional power as needed. An optional geolocation tracker 34, such as a GPS device, allows for careful monitoring of the box and enclosed vaccine during the entire delivery chain. A wireless transmitter 36 may be needed to transmit the position information back to the live monitoring system 10. The temperature sensor monitors the temperature and will provide an alert if proper temperature is exceeded, rendering the vaccine unusable. A tamper sensor ensures the box isn't opened during transit.

The box 12 would preferably include an insulating exterior layer such as EPDM rubber for enhancing temperature control within the box. The box may include multiple layers of insulation. Four layers may be enough for suitable temperature control. Preferably, the box 12 is collapsible, while retaining a rigid and free-standing orientation when deployed. The sides of the box may be selectively removable. The dimensions could range from a 48" by 24" by 15" box weighing approximately 8-10 pounds, to a 19" by 15" by 16", 5-pound size.

Chain of custody is constantly monitored, either through the wireless geolocation tracker or through other means of ensuring property transfer of the cold box 12 and enclosed vaccine 6 from one party to the next. The delivery means as indicated refers to the transportation type by which the vaccine is delivered to for the patient interaction. Live monitoring of the device ensures that the vaccine arrives intact and viable.

As explained above, once the vaccine has been applied to the patient, the post-delivery monitoring system begins. The patient and vaccine information is entered into a database which is associated with data processing to make determinations regarding vaccine distribution and effectiveness based upon post-delivery reporting by patients. External data may also be used in some cases for additional results.

Figure 3:
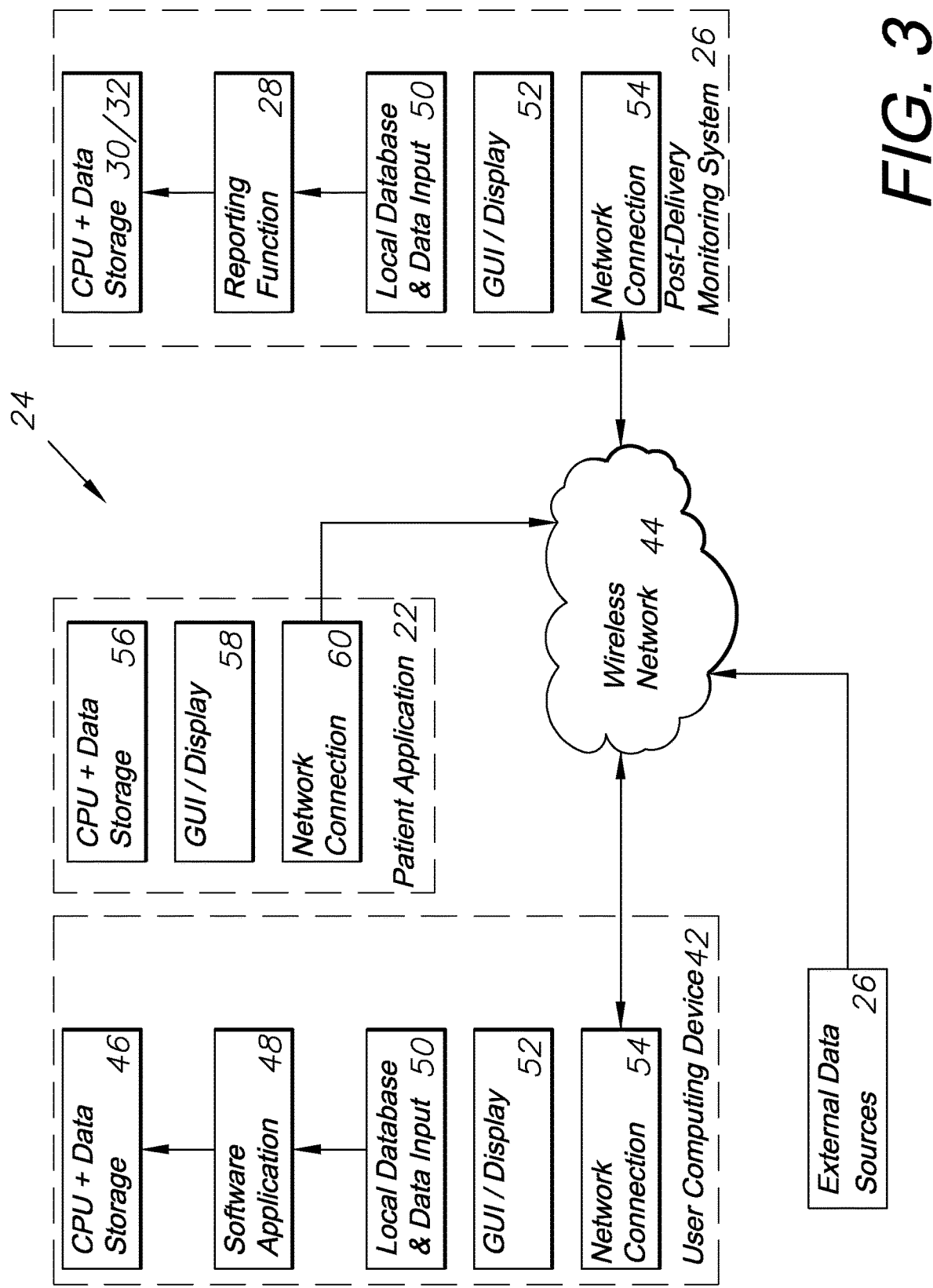
FIG. 3 is a diagram of a post-delivery monitoring system component of the present invention.

FIG. 3 shows how the post-delivery monitoring system 24 may function in an embodiment. A user computing device 42, such as a patient's smart phone, personal computer, or other computing device, includes a CPU and data storage 46, a software application 48 associated with the post-delivery monitoring, and local data input and database 50. A graphical user interface (GUI) or other interface and a display 52 are included for interaction with the computing device. A network connection 54 allows the computing device to communicate with the rest of the system 24.

Data may be self-reported from the user computing device 42 or from the site where the patient receives the patient application 22. The patient application site 22 may have a computer 56 with GUI 58 and network connection 60 to allow it to report required data to the post-delivery monitoring system 24 instead of having the patient be responsible for such reporting. This would still associate the vaccine application 22 to the specific patient/user for future monitoring.

The user computing device 42 and/or patient application site 22 communicate via a wireless network 44, such as the internet, to send relevant data to the post-delivery monitoring system 24.

The post-delivery monitoring system 24 database 32 and computer 30 receive the data inputs from the user computing device 42, the patient application 22, and/or external data sources 26 via its network connection 54. The local database and any local data input 50 is incorporated with the externally gathered data to analyze. If any reporting to the patient or other persons is required due to the data analysis, the reporting function 28 can send an alert out to the patient or other relevant party. This could include new reports about boosters or additional vaccine requirements, updates about the efficacy of the vaccine, or other relevant news or information as determined appropriate.

Cyber security aspects of the post-delivery monitoring include database security and mobile application security measures which together protect personally identifiable information, both via the app and at the database level. This would likely include full HIPAA security protection. A data security plan which includes encryption, use access plans, firewalls and data access determinations customized for each entity would be used as a part of the process.

Figure 4:
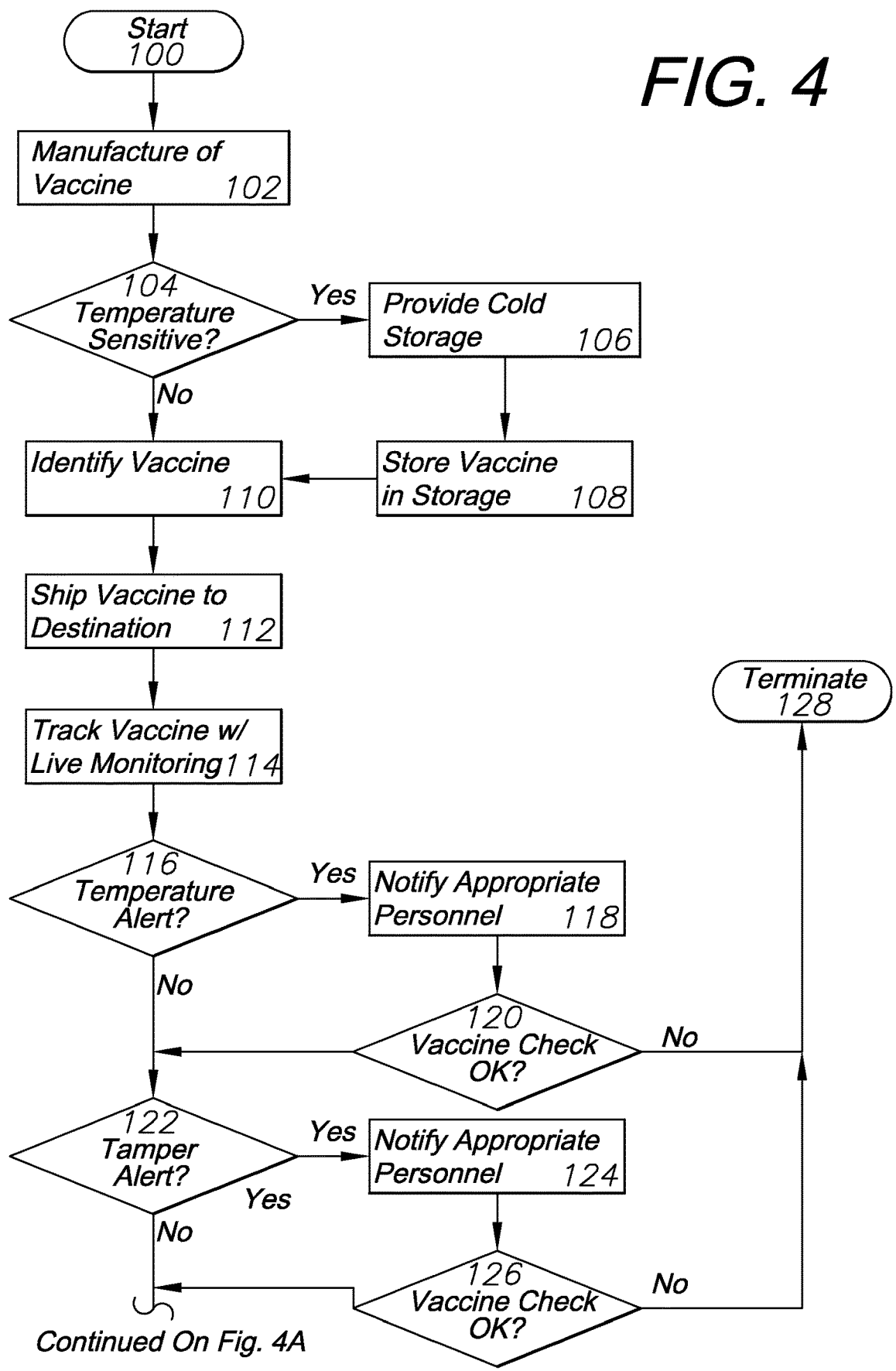
FIG. 4 is a flowchart diagramming steps taken in practicing an embodiment of the present invention.
Figure 4A:
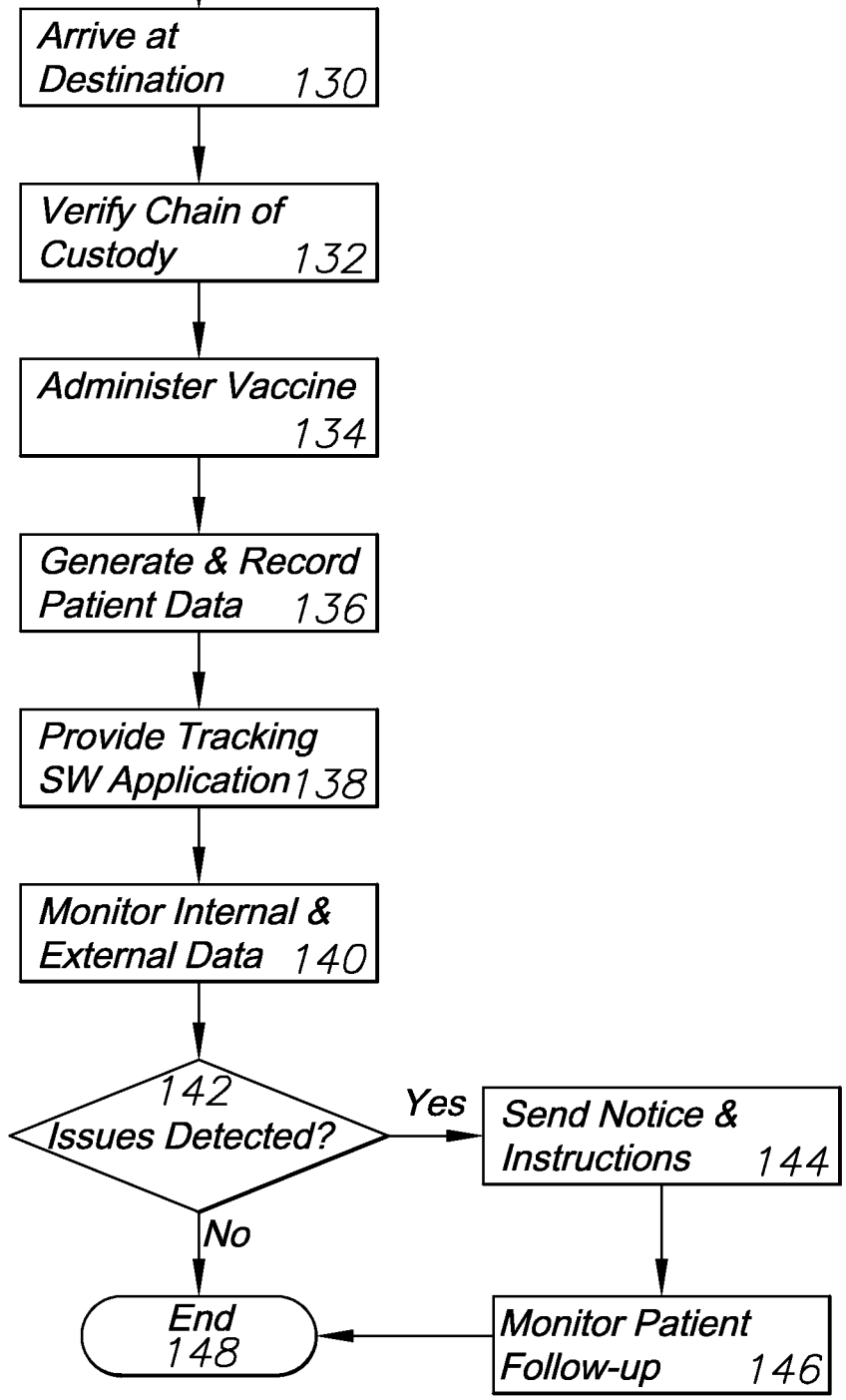
FIG. 4A is a continuation of the flowchart of FIG. 4.

FIGS. 4 and 4A step through the method for practicing the present invention as explained above. The process starts at 100 with the manufacture of a vaccine at 102. If the vaccine is temperature sensitive at 104, a cold storage box 12 may be provide at 106 and the vaccine can be stored therein at 108. The vaccine is identified and placed into the tracking system at 110 and shipped to its final destination at 112, where the live monitoring system 10 will come into play.

Tracking continues at 114 and the vaccine is constantly monitored for location, chain of custody, temperature (if needed), and tampering. If a temperature alert is determined at 116, the appropriate personnel is notified at 118 and the vaccine may be checked on site or at a remote location. If the vaccine check at 120 is not approved, the vaccine is terminated at 128 as potentially faulty. Otherwise, the process continues with a tamper check at 122. Again, the appropriate personnel is notified at 124 and the vaccine may be checked on site or at a remote location. If the vaccine check at 126 is not approved, the vaccine is terminated at 128 as potentially faulty.

Continuing on to FIG. 4A, the vaccine arrives at the destination at 130 for the patient application 22. The chain of custody is verified at 132 and, assuming approval, the vaccine will be administered to the patient at 134. The relevant patient data as associated with the vaccine is generated and recorded at 136 and the patient may be provided with the tracking software application 48 at 138 for future notifications and updates. Data is then analyzed in an on-going fashion by the post-delivery monitoring system 24 at 140. If issues are detected at 142, notice and instructions are sent to the relevant parties at 144 and, if the patient, the patient may follow-up with the notice. This follow-up is monitored by the system 24 as well at 146. Once all issues are resolved, the process ends at 148 once there are no longer any needs for updates. This could continue indefinitely.

The software tracking and monitoring the post-delivery system should include API encryption over standard AES encryption on all database data. This could be 128 bit, 192 bit, and/or 256 bit encryption. ECC should be used for mobile data encryption. SSL protocols should be employed for all web servers, and the system should separate the encrypted data and the encryption keys into distinct physical locations. For key management, hardware security modules (HSM), virtual appliances, and cloud key management services could be employed.

It is to be understood that while certain embodiments and/or aspects of the invention have been shown and described, the invention is not limited thereto and encompasses various other embodiments and aspects.

The invention claimed is:

1. A vaccine delivery and monitoring system comprising:
a live-delivery monitoring system comprising a vaccine shipping container, an automatic chain of custody monitoring system, and a shipment tracking and notification system;
said vaccine shipping container having a rectangular cross-section, said vaccine shipping container further comprising a tamper-sensor configured to generate an automated alert upon activation of said tamper-sensor;
said vaccine shipping container comprising a temperature-controlled enclosure configured to retain a temperature of said vaccine stored therein;
said vaccine shipping container further comprising a temperature sensor communicatively connected with said tracking and notification system;
said vaccine shipping container further comprising a power supply including at least one solar panel element;
wherein said temperature-controlled enclosure is configured to retain said vaccine at a temperature of thirty-two degrees Fahrenheit or lower for at least twenty-four hours;
said chain of custody monitoring system comprising digitally tracked and verified record of a chain of custody for said shipping container;
said shipment tracking and notification system comprising an automated computer system which receives updated location data of said shipping container and is configured to report said location data of said shipping container upon request;
a post-delivery monitoring system comprising a first computer having a processor and data storage, user interface, and network connection;
said post-delivery monitoring system configured to associate a vaccine stored within said vaccine shipping container and a patient assigned to the vaccine;
said post-delivery monitoring system further configured to receive post-delivery data associated with said vaccine;
said post-delivery monitoring system further configured to send a report from said post-delivery monitoring system through a reporting feature to a second computing device;
said post-delivery monitoring system further configured to send an alert from said post-delivery monitoring system to said second computing system; and
wherein said report and said alert include API encryption of at least 128 bit.

2. The system of claim 1, wherein said temperature controlled enclosure is configured to retain said vaccine at a temperature of thirty-two degrees Fahrenheit for at least thirty-six hours.

3. The system of claim 1, wherein said temperature controlled enclosure is configured to retain said vaccine at a temperature of minus twenty degrees Fahrenheit for at least twenty-four hours.

4. The system of claim 1, wherein said vaccine shipping container further comprises a geolocation tracker.

5. The system of claim 1, wherein personally identifiable information ("PII") associated with said patient is encrypted and protected within said post-delivery monitoring system.

6. The system of claim 5, wherein said PII comprises HIPAA information.

7. The system of claim 1, wherein said vaccine shipping container comprises an exterior layer of EPDM rubber.

8. A method of delivering and monitoring a vaccine, the method comprising the steps:
manufacturing a vaccine at a vaccine manufacturer;
identifying said vaccine with vaccine data;
placing said vaccine into a shipping container;
encasing said vaccine with a temperature-controlled enclosure of said shipping container, wherein said temperature-controlled enclosure is configured to retain said vaccine at a temperature of thirty-two degrees Fahrenheit or lower for at least twenty-four hours;
shipping said vaccine to a destination;
tracking said vaccine and reporting said tracking of said vaccine to a delivery monitoring system;
monitoring a tamper sensor on said shipping container to determine if said vaccine is tampered with and reporting output from said tamper sensor to said delivery monitoring system;
monitoring a temperature of said vaccine with a temperature sensor integrated into said temperature-controlled enclosure and reporting said temperature of said vaccine to said delivery monitoring system;
receiving said vaccine at a destination;
verifying chain of custody of said vaccine;
administering vaccine to a patient;

providing a tracking software application to a patient computing device associated with said patient;

monitoring internal and external data received by a post-delivery monitoring system, said post-delivery monitoring system comprising a processor, data storage, and network connection;

determining updated vaccine data with said post-delivery monitoring system from said internal and external data;

notifying said patient via said patient computing device with a notice comprising an API encryption of at least 128 bit from said post-delivery monitoring system of said updated vaccine data;

said post-delivery monitoring system further configured to send an alert from said post-delivery monitoring system to said second computing system; and communicating with said post-delivery monitoring system with said patient computing device, wherein the communication between said patient computing device and said post-delivery monitoring system comprises an API encryption of at least 128 bit.

9. The method of claim 8, wherein said temperature-controlled enclosure is configured to retain said vaccine at a temperature of thirty-two degrees Fahrenheit for at least thirty-six hours.

10. The method of claim 8, wherein said temperature-controlled enclosure is configured to retain said vaccine at a temperature of minus twenty degrees Fahrenheit for at least twenty-four hours.

11. The method of claim 8, further comprising the step: providing power to said temperature-controlled enclosure via a power supply.

12. The method of claim 11, further comprising the step: providing electrical power to said power supply via at least one solar panel.

13. The method of claim 8, further comprising the step: tracking a location of said shipping container via a geolocation tracking device located within said shipping container.

* * * * *